United States Patent [19]

Horowitz

[11] Patent Number: 4,706,652
[45] Date of Patent: Nov. 17, 1987

[54] TEMPORARY RADIATION THERAPY

[75] Inventor: Bruce S. Horowitz, Farmington Hills, Mich.

[73] Assignee: Henry Ford Hospital, Mich.

[21] Appl. No.: 814,302

[22] Filed: Dec. 30, 1985

[51] Int. Cl.⁴ .................. A61N 5/12; A61M 37/04
[52] U.S. Cl. .................................................. 128/1.2
[58] Field of Search ............................ 128/1.1, 1.2

[56] References Cited

U.S. PATENT DOCUMENTS

| | | | |
|---|---|---|---|
| 1,238,872 | 9/1917 | Bell | 128/1.1 |
| 2,829,636 | 4/1958 | Henschke | 128/1.2 |
| 3,750,653 | 8/1973 | Simon | 128/1.2 |
| 3,872,856 | 3/1975 | Clayton | 128/1.2 |
| 4,588,395 | 5/1986 | Lemelson | 128/1.2 |

OTHER PUBLICATIONS

Goffinet, PCT WO85/02779, Jul. 4, 1985.
Martinez et al., Int. J. Rod. Oncology Biol. Phys. vol. 5, No. 3, Mar. 1979, pp. 411–413.

Primary Examiner—Kyle L. Howell
Assistant Examiner—John C. Hanley
Attorney, Agent, or Firm—John Cyril Malloy

[57] ABSTRACT

A delivery system for temporary radiation therapy comprising a sheet of material which is absorbable within the human body and having a plurality of parallel passages therein. The sheet is sutured to an area of the body which is to be treated and a catheter is inserted in each passage and extends to the exterior of the body. A tube carrying a plurality of radioactive seeds dispersed therein is inserted in each catheter. After a period of treatment, the tubes and catheters are removed and the carrier remains in the body.

5 Claims, 3 Drawing Figures

U.S. Patent  Nov. 17, 1987  4,706,652
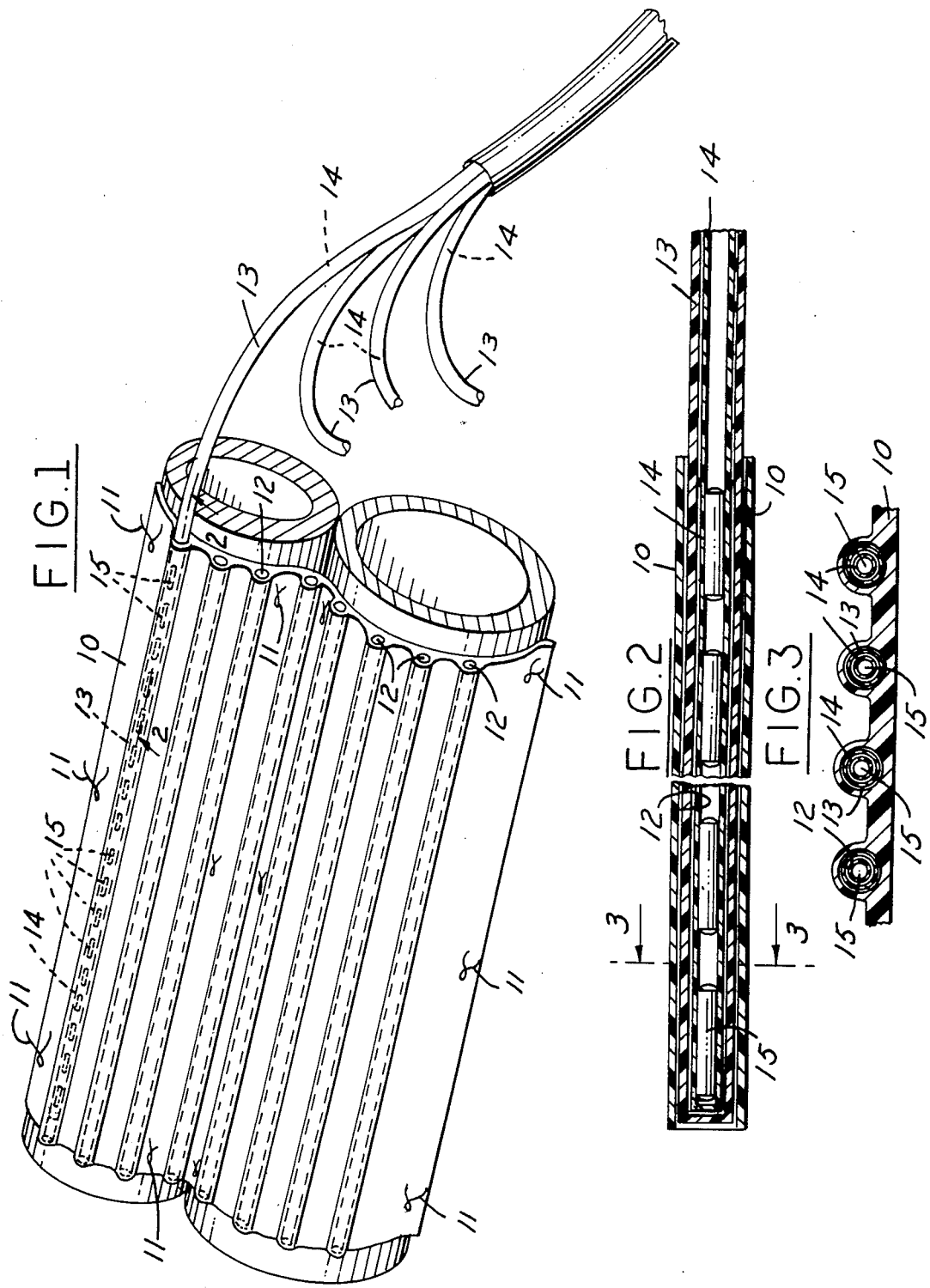

TEMPORARY RADIATION THERAPY

This invention relates to brachytherapy and particularly to temporary radiation and therapy and a delivery system for temporary radiation therapy.

BACKGROUND AND SUMMARY OF THE INVENTION

Interstitial radiation therapy has been performed since the beginning of the 20th Century. Radium was developed by Madam Curie and Alexander Graham Bell proposed the use of radium in tumors. Subsequently, metal needles were developed in which a radium isotope was encapsulated for insertion in close proximity or into tumors. Where the tumor was deep seated, an operation was necessary to provide access to the tumor. Such therapy had serious problems and disadvantages. The high energy of the radium isotope required a great deal of shielding and subjected the personnel to harmful exposure. In addition, the needles tended to break as they aged resulting in the release of the radioactive contents. Since the radium isotopes had a half-life of about 1600 years, they produced an extreme contamination hazard.

Thus, efforts have been made to develop more effective brachytherapy which is safer and more convenient to use. This has resulted in the development of radioactive materials that have lower energies and thus require less shielding and have shorter half-lives to reduce the risk of contamination. Thus, permanent seeds of encapsulated radon-222 having an energy level of 0.78 MEV and a half-life of 33.83 days or of encapsulated gold-198 having an energy level of 0.42 MEV and a half-life of 2.7 days have been used. More recently small seeds of iridium-192 having an energy level of 0.30 MEV and a half-life of 74.2 days and iodine-125 having an energy level of 0.028 MEV and a half-life of 60 days have been developed. Such seeds are shown, for example, in U.S. Pat. Nos. 3,351,049 and 4,323,055.

Such iridium and iodine seeds are on the order of 4.5 mm in length and 0.8 mm in diameter and are implanted in the tumor or placed in the surface of the tumor. Both of these sources have lower energies than radium that allow for simpler shielding and less radiation exposure to personnel. With seeds of iodine encapsulated in a material such as titanium, shielding is provided by the surrounding tissue and the seeds can be left in the patient permanently without the need for major precautions.

Further development in brachytherapy has been the development of techniques for implanting the newer developed radioactive seeds. Two techniques, in general, have been developed to allow further reduction in personnel exposure during the implanting process. The two techniques involved are permanent and temporary implants. Both utilize afterloading techniques where guides in the form of catheters are placed through the tumor mass or on the tumor surface.

Permanent implants usually use sources with a very short half life of a few days or low energy low activity, both resulting in very low exposure to bystanders so the patient can be discharged without fear. Since loose radioactive seeds are utilized, this procedure can only be used by volume implants in an effort to firmly hold the seeds in place. Problems arise if an implant is needed in a volume that will not be able to sustain the seeds in a rigid geometrical position, such as a breast tumor where the breast tissue is flexible. Likewise, the tumor volume only represents a thin layer of tumor cell. Examples include tumors that grow over the surface but invade only minimally the skin or a flat plexus of vessels containing tumor such as the tumor barring lymphatics of the mediastium or the tumor bed when a tumor is removed off of a surface which still harbors malignant cells. This type of implant usually requires a supporting carrier for the radioactive seeds, which must be removed within a specified time, neccessitating a temporary implant. Thus in this technique nylon plastic catheters are sutured on, or pierced through, the tumor volume. The catheters are then loaded by inserting a second nylon catheter of a smaller diameter containing the radioactive seeds. After the desired radiation dose is delivered the two catheters are withdrawn.

The temporary catheter placement for treatment of tumor beds has an ever increasing role in cancer management, as mutilating surgical procedures decrease and post operative irradiation is utilized to treat the scattered cancer cell. Thus the use of placing temporary iridium implants as described above has found a significant role in the treatment of lung tumors. Tumors frequently have to be sharply dissected off of the chest wall, diaphragm, or the central vital organs of the chest. Colon and rectal tumors frequently have to be dissected off of the pelvic bony wall. Although this technique does work, there are inherent problems that this innovation solves while other techniques attempting to solve the problem do not address all the to be described difficulties and do not solve them.

As described above the technique for temporary planar implants involves the suturing of nylon catheters to the tumor bed after the removal of the cancer while the patient is under general anesthesia. The method is well described by Hilaris et al, "Value of Perioperative Brachytherapy in the Management of Non-Oat Cell Carcinoma of the Lungs", *Int. J. Radiation Oncology Biol. Phys.*; Vol. 9, pp. 1161–1166, (1983). Each catheter should be sutured in three to four places. This is a time consuming procedure which uses expensive operating time as well as increasing the patient's risks. This problem is compounded if the implant needs to be performed in a tight area or awkward position. The catheters cannot be sutured at all when removal of the tumor is so complete as not to leave tissue to suture the catheters to. An example of this would include a pelvic tumor removed leaving only pelvic bone riddled with cancer cells. Since these catheters are anchored in only at a few points along their path, yet need to follow a irregular surface, the catheters tend to lose the parallel spacing between them, resulting in areas where the catheters become bunched together, and a resultant relative hot spot and causing radiation overdose with necrosis, while leaving an area of underdosage where a tumor recurrence can occur. An overdose over a critical area such as the spinal cord can leave a patient crippled for life, while tumor recurrence will cause the patient's death.

Another technique described by Martinez et al, "Sterilization of $^{125}$I Seeds Encased in Vicryl Sutures for Permanent Interstitial Implementation", *Int. J. Radiation Oncology Biol. Phys.*; Vol. 5, pp. 411–413 (1979) utilizes Iodine-125 seeds spaced within a braided absorbable polymer surgical suture (Vicryl). Although this technique allows for a permanent planar implant in areas described above, still maintains the many of the above problems of time consumption of placing individual sutures, including inability to implant denuded areas, and ability to maintain exact parallelism between the ribbons.

Another technique by Marchese et al, "A Versatile Permanent Planar Implant Technique Utilizing Iodine-125 Seeds Imbedded in Gelfoam", *Int. J. Radiation Oncology Biol. Phys.*; Vol. 10, pp. 747–751 (1984) again utilized absorbable materials and Iodine-125 seeds to perform a permanent planer radioactive implant. This technique utilizes commercially available absorbable polymer mesh and putty material. At the time the surgical debulking of tumor, the mesh is cut to conform to the tumor bed, the putty is flattened into pancake fashion, and the seeds are placed into the putty, at a predetermined spacing then placed on the mesh which is sutured over the tumor bearing surface. Although this solves the problem of planar implants over denuded areas, and reduces actual suturing time, new problems are created. First, since the pancake style implant can only be manufactured after the tumor is removed and the shape of the tumor bed is known, and since it has to be manufactured under sterile conditions, the end result is a greatly extended operating time while the pancake is being prepared. Another problem is there is no quality assurance of the thickness of the pancake holding the radioactive seeds, and thus in thin areas the material will be absorbed quickly resulting in premature release of the seeds, underdose in that area, and recurrence of tumor.

It is also noted in the techniques of Hilaris and Martinez above that the seeds are low dose rate, and would not be applicable in a rapidly proliferating tumor system.

Accordingly, among the objectives of the present invention are to provide a delivery system for temporary radiation therapy which obviates the aforementioned disadvantages and holds the seeds in accurate position to provide the desired radiation therapy.

In accordance with the invention, the delivery system comprises a carrier in the form of a sheet of absorbable material which has a plurality of passages. The sheet is sutured adjacent the area to be treated and a catheter is inserted in each passage. A tube containing a plurality of radioactive seeds is inserted in each catheter. After the desired treatment, the tubes and catheters are removed leaving the carrier in the body.

DESCRIPTION OF THE DRAWINGS

FIG. 1 is a partly diagrammatic perspective view of the delivery system embodying the invention.

FIG. 2 is a sectional view taken along the line 2—2 in FIG. 1.

FIG. 3 is a sectional view taken along the line 3—3 in FIG. 1.

DESCRIPTION

Referring to the drawings, the delivery system embodying the invention comprises a carrier in the form of a flexible sheet 10 of absorbable material which is sutured as at 11 adjacent the area which is to be treated. Sheet 10 conforms to the surface to be treated. Sheet 10 includes a plurality of parallel straight passages 12 extending substantially to the edges of the sheet. One end of the passages is preferably sealed.

A plurality of catheters 13 are inserted in the ends of passages 12. A plurality of tubes 14, carrying longitudinally spaced radioactive seeds 15 held therein by friction, are inserted in the catheters 13 and extend through the skin of the body to the exterior.

The sheet may be made of any of the natural or synthetic absorbable materials. An example of a natural absorbable material that may be used to produce the conformable sheets of the present invention is collagen. Examples of suitable synthetic absorbable materials are the polyester amides derived froom glycolic or lactic acids such as the polymers and copolymers of glycolide and lactide, polydioxanone and the like. Such polymeric materials are more fully described in U.S. Pat. Nos. 3,565,869, 3,636,956, 4,052,988 and European Patent Application No. 30822. Specific examples of such polymers are sold by ETHICON, Inc., Somerville, N.J., under the trademarks "VICRYL" and "PDS".

The absorbable material should preferably maintain its integrity for from 1 to 14 days. Preferably the material should be absorbed in living tissue in a period of time of from about 70 to 120 days. It is preferred that as little absorbable material as possible be used in the delivery system of the present invention. The sheet may be a cast sheet, extruded sheet, woven sheet, non-woven sheet or the like.

The catheters may be made of nylon.

In a typical application, sheet 10 has a thickness of 0.020 inch, catheters have an O.D. of 0.085 inch and an I.D. of 0.070 inch, and tubes 14 have an O.D. of 0.060 inch and an I.D. of 0.045 inch, and tubes 14 have an O.D. of 0.035 inch and an I.D. of 0.032 inch.

The seeds can be of various types having low energy and low half life such as iodine seeds, known as I-125 seeds or iridium seeds, known as Ir-192 seeds.

In a typical application, the following steps are performed:

1. The tumor bed is exposed by appropriate surgical technique.

2. The absorbable carrier 10 is cut to conform to the tumor bed.

3. The carrier is sutured using a minimum of six absorbable or non-absorbable sutures.

4. A catheter 13 is inserted in each passage 12 of the carrier 10 and the other end of the catheter extends through the skin through a separate incision. A purse string suture is placed around the suture.

5. The incision is closed.

6. After approximately 2 days and not more than 10 days, tubes 15 carrying "dummy" seed ribbons are inserted and orthogonal radiographs are made for dosimetric purposes. Using a proper computer program, the isodoses are drawn. Tubes 15 carrying radioactive seeds such as Ir 192 are inserted in the catheters 12. The activity per seed should be such as to deliver approximately 1000 rads per day to the isodose that encompasses a plane one-half centimeter from and parallel to the plane of implant.

7. After the proper dose is delivered to the selected isodose line on the graph, the tubes 15 carrying the seeds are removed. The catheters 13 are then removed and the suture at the skin is pulled tight to close the incision.

The advantages of the absorbable template are:

1. Fixed parallel spacing of catheters to decrease hot and cold spots.

2. Reduced surgical time, since an array of catheters can be sutured in place instead of individual catheters.

3. Spaces normal tissues away from the seed surface to decrease necrosis from a high local dose.

4. Allows attachment over denuded or inaccessible areas where suturing would be difficult or impossible.

5. A temporary planer implant for tumor bed irradiation has the additional advantage of allowing for the temporary displacement of normal structures, thus decreasing normal tissue irradiation. An example would be the displacement of small bowel when irradiating the pelvic floor after removal of sigmoid carcinoma.

6. Permits the controlled and safe use of high dose rate seeds.

What is claimed is:

1. A carrier for temporary radiation therapy comprising
    a flexible sheet of a material absorbable by the human body,
    said sheet having a plurality of generally parallel passages therein,
    a catheter extending into each said passage,
    a tube containing longitudinally spaced radioactive seeds extending into each said catheter.

2. The carrier set forth in claim 1 wherein said sheet comprises a polymer.

3. The carrier set forth in claim 2 wherein said carrier comprises polydioxanone.

4. The carrier set forth in claim 2 including means on each said catheter for frictionally engaging the end of the passage.

5. The carrier set forth in claim 2 wherein one end of each said passage is closed.

* * * * *